United States Patent [19]

Ashmead

[11] 4,216,144

[45] Aug. 5, 1980

[54] SOLUBLE IRON PROTEINATES

[76] Inventor: Harvey H. Ashmead, P.O. Box 750, Clearfield, Utah 84015

[21] Appl. No.: 843,972

[22] Filed: Oct. 20, 1977

[51] Int. Cl.² ............................................... C07G 7/04
[52] U.S. Cl. ........................................ 260/115; 71/15; 71/23; 71/27; 260/112.5 R; 260/429 J; 424/177; 426/656; 562/553; 562/567
[58] Field of Search ................ 260/113, 115, 112.5 R, 260/429 J; 562/553, 567

[56] References Cited

U.S. PATENT DOCUMENTS

| | | | |
|---|---|---|---|
| 1,027,967 | 5/1912 | Zuckmayer | 260/115 |
| 3,344,130 | 9/1967 | Mortenson | 260/115 |
| 3,396,104 | 8/1968 | Miller | 210/54 |
| 3,637,640 | 1/1972 | Huber | 260/115 |
| 3,775,132 | 11/1973 | Richards | 426/364 |
| 3,823,127 | 7/1974 | Jones et al. | 260/112 R |
| 3,969,540 | 7/1976 | Jensen | 426/657 |
| 4,020,158 | 4/1977 | Ashmead et al. | 424/177 |

*Primary Examiner*—Walter C. Danison
*Attorney, Agent, or Firm*—Criddle & Western

[57] ABSTRACT

Iron proteinates or chelates of iron with hydrolyzed protein which are usually insoluble are rendered soluble without destroying the chelate and are more readily assimilable by plants and animals.

4 Claims, No Drawings

SOLUBLE IRON PROTEINATES

BACKGROUND OF THE INVENTION

Metal amino acid or protein hydrolysate chelates have been referred to in the art as being water insoluble metal proteinates containing at least two ligands per metal ion present. They are described as such in U.S. Pat. No. 4,020,158; U.S. Pat. No. 3,969,540; U.S. Pat. No. 3,775,132, and U.S. Pat. No. 3,396,104.

The proteinate is formed by complexing a protein hydrolysate having protons removed therefrom by pH adjustment until the hydrolysate molecule is electronegative. The electron rich hydrolysate is then reacted with an iron ion to form a "claw-like" structure known as a chelate.

The chelate is formed by first dissolving a water soluble iron salt in water. The iron ion will have a valence of plus two or three but that does not define all of the reaction sites of the ion. The ion will contain a certain but varying number of waters of hydration known as coordination complexes that may be represented by the following formula using a ferrous ion and four waters of hydration.

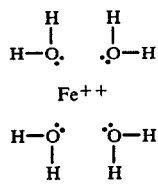

Using glycine as the simplist protein hydrolysate it will exist as a zwitterion at its isoelectric point and have the formula:

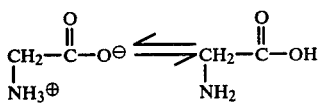

Upon raising the pH, the protons are removed leaving an electronegative hydrolysate or the formula:

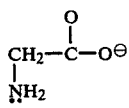

By combining the electronegative protein hydrolysate with a metal ion the following reaction is thought to initially occur:

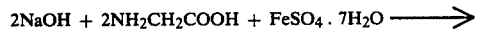
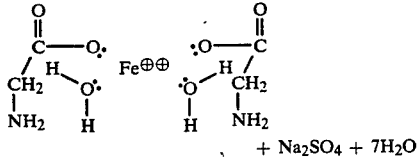

$+ Na_2SO_4 + 7H_2O$

Upon the addition of more base (NaOH) the product becomes a chelate having the formula:

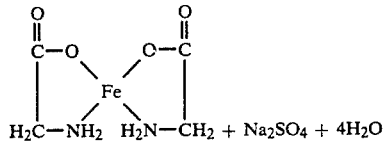

$+ Na_2SO_4 + 4H_2O$

It will be noted that the iron is completely protected from ionization and has a relatively high stability constant on the order of $10^{7-12}$. The citrates and ascorbates form much weaker chelate bonds on the order of $10^{2-4}$ and EDTA (ethylenediaminetetraaceticacid) and its derivatives form a strong chelate having a stability constant on the order of $10^{16-28}$. The citrates and ascorbates tend to decompose before they can be assimilated into a biological system and it is much more difficult to absorb a positive metal ion than a chelate. EDTA and its derivatives form such strong chelate bonds that they pass intact through most biological systems whether they be plants or animals, including humans. For this reason EDTA is often administered as a metal scavenger to remove unwanted metal ions from biological systems. Iron proteinates are sufficiently stable that they are absorbed into biological systems where the chelate bonding is broken and the iron ion and amino acid are utilized by the biological system at the appropriate place. In an animal for example, most absorption of iron in the chelate form occurs in the small intestine. The iron proteinate then must be sufficiently stable to pass through the acidic stomach media into the small intestine.

In the past, iron proteinates have been insoluble and have been mixed with food or administered in tablet or capsule form. This may not be convenient when using them for plants and animals including man.

DESCRIPTION OF THE INVENTION

It has now been found that iron proteinates may be made in soluble form. The iron proteinate is a true chelate but is a different type of chelate than previously described.

Water soluble iron proteinates are unexpected in view of the prior art and are valuable in that they permit the dispensing of iron proteinates by more convenient methods. For example, soluble iron proteinates may be added to the drinking water of animals, including humans. They may also be used as foliar sprays to overcome deficiencies of iron in plants. They may also be applied to the soil prior to or after germination of plant seeds. However applied, they greatly increase the metal absorption in both plant and animal tissues. Another advantage is that the soluble iron proteinates may be easily incorporated into foodstuffs, especially bakery products.

The iron proteinate has been demonstrated by analysis to be at least 70 to 80 percent chelated and be sufficiently water soluble to provide a solution containing 30 to 40 percent solids of which about five to seven percent is iron and the remainder protein hydrolysate.

A solution of soluble iron proteinates may be dried and reconstituted or dissolved. Thus this product may be shipped dry without the necessity of having to ship aqueous solutions thereby incurring greater shipping costs.

The iron must contain at least three ligands per iron ion regardless of its oxidation state. Preferable between three and six ligands are used. The pH of the reaction solution must be carefully controlled. At an acidic pH i.e. below 7, only a salt will be formed. At too alkaline a pH, i.e. above about 8, a precipitate will form. The reaction takes place in solution using a soluble iron salt. Preferrably a hydrated iron sulfate ($FeSO_4.xH_2O$) wherein x is an interger from one to nine or an iron halide such as iron chloride ($FeCl_2.xH_2O$ or $FeCl_3.xH_2O$) wherein x is an interger from zero to six. The use of other slats is not precluded. The reaction is thought to product a chelate having one of the following formulas using glycine as the ligand:

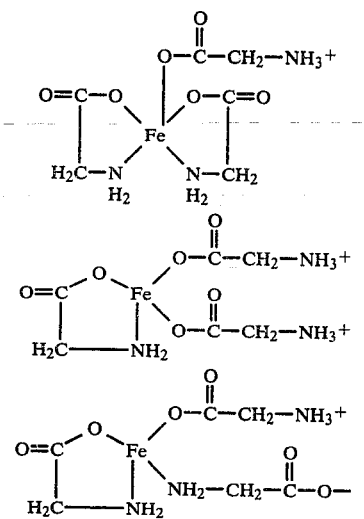

It will be noted in each of the above formulas that the iron atom is completely neutralized having no positive charge on the iron. This is very important since iron ions are often repelled in a biological system. This is particularly true in humans wherein the RDA (recommended daily allowance) is 18 mg. Only about two mg. of iron are absorbed if the iron is administered in a form other than a iron proteinate. Soluble iron proteinates are unique from other soluble metal proteinates in that they remain soluble over only a two to three day period and thus must be used within a relatively short period of time after being solubilized. Other soluble metal proteinates are found in our copending application Ser. No. 843,969 filed Oct. 20, 1977, and cannot be prepared form sulfate or chloride salts as can the iron product but when prepared are soluble over a prolonged period of time.

As mentioned at a pH above about 8, the soluble iron proteinate will precipitate. This is due to the excess proton being removed from the amino group.

Any suitable protein source may be used to form the hydrolysate. Isolated soy protein may be hydrolyzed as may albumen, gelatin or any other product capable of producing polypeptides, peptides and naturally occurring amino acids. Such natural amino acids include alanine, arginine, aspartic acid, cystine, diiodotyrosine, glutamic acid, glycine, histidine, hydroxproline, isoleucine, leucine, lysine, methionine, phenylalanine, proline, serine, threonine, thyroxine, tryptophan, tyrosine, valine, aspartamine and glutamine.

A peptide or polypeptide may be made from a combination of two or more like or different amino acids and may have a configuration ranging from two glycine molecules up to polypeptide chains having molecular weights in the thousands or hundreds of thousands. The stereo configuration will dictate the structure formed. In general the shorter the chain length the more soluble the proteinate will be.

The iron atom, whether ferrous or ferric, will be more readily absorbed in liquid form than as a precipitate. In order to maintain the pH a buffer system may be employed. When used for human consumption between about two to eighteen mg. of iron in the form of a soluble proteinate may be used on a daily basis. For plant application between one to four pounds of iron as a soluble iron proteinate may be applied per acre on each application. When used for animals other than humans, the dosage will ordinarily vary from about 0.03 to 3.0 mg/kg of body weight on a daily basis.

EXAMPLE I

Twenty seven grams (0.1 mole) of $FeSO_4 \cdot 7H_2O$ were added to 100 mls of water. This mixture was heated to 60° C. and stirred to bring the ferrous sulfate into solution. To this solution was added 61 grams (0.3 moles of amino acids) as hydrolyzed vegetable protein. This solution was heated and stirred at 80° C. for 20 minutes. After cooling to 50° C., 5.6 grams (0.1 mole) of potassium hydroxide was added with stirring. The pH of the solution has between about 7.1 to 7.8 and all the ingredients were soluble. The solution was dried in a thin film evaporator at 60° C. and stored for several days. The resulting product was soluble when reconstituted with water. Upon analysis it was found that the ferrous ion was about 70 percent chelated. The resulting product contained about 5–6 percent by weight iron.

EXAMPLE 2

A solution containing 36 mg of iron as soluble iron proteinate was added to a bread dough mixture and well mixed in during the mixing of ingredients. One loaf of bread dough was formed which was baked, cooled, and sliced into 18 slices. Each slice contained about 2 mg. of iron as iron proteinate.

EXAMPLE 3

A solution of soluble iron proteinates containing 18 mg. of iron per 8 oz. of solution was tested against a control of 18 mg. of iron sulfate dissolved in 8 oz. of water. Twelve human volunteers divided into two groups were examined for blood hemoglobin content at the beginning of the test. Each volunteer consumed 8 oz. of sample daily over a period of fifteen days. Blood hemoglobin tests were again run and the group taking the soluble iron proteinate had an increased hemoglobin count of twelve percent wherein the control group showed an increase in blood hemoglobin of only 2.5 percent.

EXAMPLE 4

Thirty hampsters were divided into two equal groups. A hair sample from the belly of each hampster was analyzed and averaged for each group. One group of hampsters were watered for thirty days using a solution containing 0.5 mg. of iron as iron sulfate per ounce of water. The second group of hampsters received the same amount of iron as a soluble iron proteinate per ounce of water. After thirty days a hair sample was again taken from the same place. The iron content in the hair of the control group showed negligible change whereas the iron content in the group treated with the soluble iron proteinate showed a sixteen percent increase in iron content.

EXAMPLE 5

Soluble iron proteinates as a foliar spray were applied to wheat as follows. Five pounds of hard red wheat was rinsed with distilled water three times to remove external contamination. The wheat was soaked twelve hours in distilled water. The wheat was then placed on six trays with automatic watering. Distilled water was again used.

After 10 days the wheat had sprouted to about five inches in height. Tray No. 3 was designated as the control. All other trays were sprayed with an iron proteinate solution. Ten cc. of iron proteinate would calculate to one pound of iron as the iron proteinate diluted to 200 gallons of water and sprayed on one acre. Twenty cc would be equivalent to two pounds per acre of iron as an iron proteinate. One to two pounds of iron per acre are considered to be optimum. One day later one-half of each tray was removed and the remaining half was sprayed with the same amount of iron as used on the entire tray on day ten. On the twelfth day, the plants were washed, dried, and assayed for iron content with the results being reported in terms of mgs. of iron per gram of dried plant.

|     |          |                    | Iron mg/gm |       |
|-----|----------|--------------------|------------|-------|
| Day | Tray No. | Volume Spray Used  | Leaves     | Roots |
| 10  | 3        | 10 cc H₂O          | 0.15       | 0.45  |
| 10  | 1        | 10 cc Fe Proteinate| 0.21       | 0.19  |
| 10  | 2        | 20 cc Fe Proteinate| 0.45       | 0.24  |
| 11  | 1        | 10 cc Fe Proteinate| 0.28       | —     |
| 11  | 2        | 20 cc Fe Proteinate| 0.83       | —     |

The rate of iron absorption through the wheat sprouts is clearly superior to the control. Spraying with 2 lbs per acre increased blade absorption three times in 10 days as compared to the control. The application on day 10 amounted to 2 and 4 lbs. of iron per acre as a proteinate. After just one day, the absorption of 2 lb. per acre of spray increased absorption about 50% whereas the 4 lb. per acre application nearly doubled the iron absorption i.e. from 0.45 to 0.83 mg/gm of dried material.

EXAMPLE 6

A more elaborate test using $Fe^{59}$ was conducted using three solutions. A stock solution was prepared dissolving 7.95 gm per liter of $FeSO_4.7H_2O$. Forty mls of this solution was diluted with 160 mls of distilled $H_2O$.

Solution 1 was an iron proteinate containing at least three ligands per iron atom made by dissolving 10 parts by volume of stock solution with 10 parts by volume of a soluble hydrolyzed vegetable protein solution (HVP), 10 parts by volume of 1.0 N KOH and 10 parts by volume of distilled $H^2O$. The pH was about 7.3.

Solution 2 was an EDTA-2Na (disodium salt of ethylenediamenetetracetic acid) chelate made by dissolving 10 parts by volume of stock solution with 20 parts by volume of EDTA-2Na, containing one gram of ligand per liter of water, and 10 parts by volume of $H_2O$.

Solution 3 was a control solution containing 10 parts by volume of stock solution and 30 parts by volume of distilled water.

Tomato plants in the six leaf stage were used. Forty microliters of solution was placed on one leaf of each plant. After three days the leaf was excised and dried. The $Fe^{59}$ in each case was counted on a standard nuclear counter and the results reported in terms of corrected counts per minute per milligram (cc/min/mg). Three replicates were made using each solution. The results were averaged as follows:

| Solution 1    | Solution 2   | Solution 3                |
|---------------|--------------|---------------------------|
| Fe Proteinate | EDTA Chelate | Control (FeSO₄)           |
| 43.09         | 26.63        | 29.42                     |

It can clearly be seen that the Fe Proteinate is far superior to the EDTA chelate which is sometimes used. In fact, the EDTA chelate was not as effective as the inorganic ferrous sulfate solution.

I claim:

1. An iron proteinate having a water solubility sufficient to provide an aqueous solution containing at least five precent by weight iron at ambient temperatures at a pH of between about 7 and 8 comprising an iron ion in co-ordination complex with at least three protein hydrolysate ligands selected from the group consisting of polypeptides, peptides and naturally occurring amino acids wherein at least one of the ligands contains an amino group having an excess proton.

2. A soluble iron proteinate according to claim 1 wherein the iron ion is a ferric ion.

3. A soluble iron proteinate according to claim 1 wherein the iron ion is a ferrous ion.

4. A soluble iron proteinate according to claim 1 wherein the proteinate contains three ligands.

* * * * *